(12) United States Patent
Iwai et al.

(10) Patent No.: US 12,390,652 B2
(45) Date of Patent: Aug. 19, 2025

(54) AUTOMATED EXTERNAL DEFIBRILLATOR

(71) Applicant: Nihon Kohden Corporation, Tokyo (JP)

(72) Inventors: Fumihito Iwai, Saitama (JP); Yutaka Uchiyama, Saitama (JP)

(73) Assignee: Nihon Kohden Corporation, Tokyo (JP)

( * ) Notice: Subject to any disclaimer, the term of this patent is extended or adjusted under 35 U.S.C. 154(b) by 383 days.

(21) Appl. No.: 18/008,078

(22) PCT Filed: Apr. 28, 2021

(86) PCT No.: PCT/JP2021/017003
§ 371 (c)(1),
(2) Date: Dec. 2, 2022

(87) PCT Pub. No.: WO2021/256101
PCT Pub. Date: Dec. 23, 2021

(65) Prior Publication Data
US 2023/0310872 A1    Oct. 5, 2023

(30) Foreign Application Priority Data

Jun. 15, 2020 (JP) .................... 2020-103070

(51) Int. Cl.
*A61N 1/39* (2006.01)
*A61N 1/04* (2006.01)
*H05K 1/02* (2006.01)

(52) U.S. Cl.
CPC ........... *A61N 1/3904* (2017.08); *A61N 1/046* (2013.01); *A61N 1/3968* (2013.01); *H05K 1/0256* (2013.01); *H05K 2203/1327* (2013.01)

(58) Field of Classification Search
CPC .... A61N 1/3904; A61N 1/3968; H05K 1/056; H05K 2203/1327
See application file for complete search history.

(56) References Cited

U.S. PATENT DOCUMENTS 3,867,950 A * 2/1975 Fischell ............... A61N 1/3787
320/137
6,614,108 B1 * 9/2003 Sanftleben ............. H01L 23/10
257/710

(Continued)

FOREIGN PATENT DOCUMENTS

EP    1796790 A1    6/2007
EP    3603743 A1    2/2020

(Continued)

OTHER PUBLICATIONS

International Search Report and Written Opinion issued in International Application No. PCT/JP2021/017003, mailed on Aug. 4, 2021, 7 pages.

(Continued)

*Primary Examiner* — Eric D. Bertram
(74) *Attorney, Agent, or Firm* — Dorsey & Whitney LLP

(57) ABSTRACT

An automated external defibrillator includes: a high voltage generator configured to charge or discharge electric energy for giving a subject an electric shock for defibrillation; an outer housing configured to house the high voltage generator and defining an exterior of the automated external defibrillator; and a potting material containing an insulating material. The high voltage generator includes: a high voltage circuit board; and a high voltage electronic component disposed on the high voltage circuit board. The potting material covers the high voltage circuit board and a terminal of the high voltage electronic component, and is in contact with the high voltage circuit board and the outer housing to fix the high voltage circuit board to the outer housing.

7 Claims, 5 Drawing Sheets

(56) References Cited

U.S. PATENT DOCUMENTS

| | | | |
|---|---|---|---|
| 7,865,238 B2* | 1/2011 | Brink | A61N 1/3904 607/7 |
| 9,427,564 B2* | 8/2016 | Kaib | A61N 1/3993 |
| 2005/0264979 A1* | 12/2005 | Breyen | H01G 9/004 361/517 |
| 2006/0058846 A1 | 3/2006 | Smirles et al. | |
| 2007/0010134 A1* | 1/2007 | Powers | A61N 1/3968 439/620.09 |
| 2007/0213776 A1* | 9/2007 | Brink | A61N 1/3904 607/7 |
| 2007/0299474 A1* | 12/2007 | Brink | A61N 1/3904 607/7 |
| 2019/0159696 A1 | 5/2019 | Meeker et al. | |
| 2021/0069510 A1* | 3/2021 | Swoyer | A61N 1/36178 |
| 2021/0308473 A1 | 10/2021 | Doerr et al. | |

FOREIGN PATENT DOCUMENTS

| | | |
|---|---|---|
| JP | H02256202 A | 10/1990 |
| JP | 2001015358 A | 1/2001 |
| JP | 2002303423 A | 10/2002 |
| JP | 2006516208 A | 6/2006 |
| JP | 2007311706 A | 11/2007 |
| JP | 2008514329 A | 5/2008 |
| JP | 2014053083 | 3/2014 |
| WO | 2006035334 A1 | 4/2006 |
| WO | 2021256101 A1 | 12/2021 |

OTHER PUBLICATIONS

Office Action issued in Japanese Patent Application No. 2020-103070 issued on Jan. 16, 2024, 5 pages including 3 pages of English translation.

* cited by examiner

AUTOMATED EXTERNAL DEFIBRILLATOR

This application is a 371 national phase entry of International Application PCT/JP2021/017003 filed on Apr. 28, 2021 which in turn claims priority to Japanese Patent Application No. 2020-103070 filed on Jun. 15, 2020, the entire contents of which are incorporated herein by reference.

TECHNICAL FIELD

The present disclosure relates to an automated external defibrillator.

BACKGROUND ART

Recently, automated external defibrillators (hereinafter abbreviated to AEDs) are rapidly spreading. Such an AED gives a strong electric shock for defibrillation to a heart of a patient who has undergone sudden cardiac arrest due to ventricular fibrillation, to thereby restore a function of the heart of the patient. The AED is provided with a high voltage circuit which can control charging and discharging of electric energy for giving the patient the electric shock for defibrillation (e.g. see JP-A-2008-514329). The high voltage circuit disclosed in JP-A-2008-514329 is housed in a housing for a high voltage module. In order to ensure electrical insulation among terminals of electronic components provided on the high voltage circuit, the housing in which the high voltage circuit has been housed is filled with a dielectric material (potting material) such as an epoxy resin. In this manner, the high voltage module provided with the high voltage circuit embedded in the dielectric material is manufactured.

SUMMARY

The high voltage module disclosed in JP-A-2008-514329 is housed in an outer housing of the AED, and fixed to the outer housing through a mechanical fixature (such as a screw). Therefore, there is a possibility that when a strong impact is applied to the AED from the outside, large force is applied to a connection portion between the high voltage module and the outer housing. Further, since it is necessary to provide a certain clearance between an outer wall of the outer housing and the high voltage module, an external size of the AED increases. Thus, there is room for improvement of the AED from a viewpoint of durability and the external size of the AED The present disclosure is directed to improving durability of an AED and miniaturizing the AED According to one or more aspects of the present disclosure, there is provided an automated external defibrillator. The automated external defibrillator includes: a high voltage generator configured to charge or discharge electric energy for giving a subject an electric shock for defibrillation; an outer housing configured to house the high voltage generator and defining an exterior of the automated external defibrillator; and a potting material containing an insulating material. The high voltage generator includes: a high voltage circuit board; and a high voltage electronic component disposed on the high voltage circuit board. The potting material covers the high voltage circuit board and a terminal of the high voltage electronic component, and is in contact with the high voltage circuit board and the outer housing to fix the high voltage circuit board to the outer housing.

DESCRIPTION OF EMBODIMENT

An embodiment will be described below with reference to the drawings. Dimensions of each member shown in each drawing may be different from actual dimensions of the member for convenience of explanation.

Figure 3:
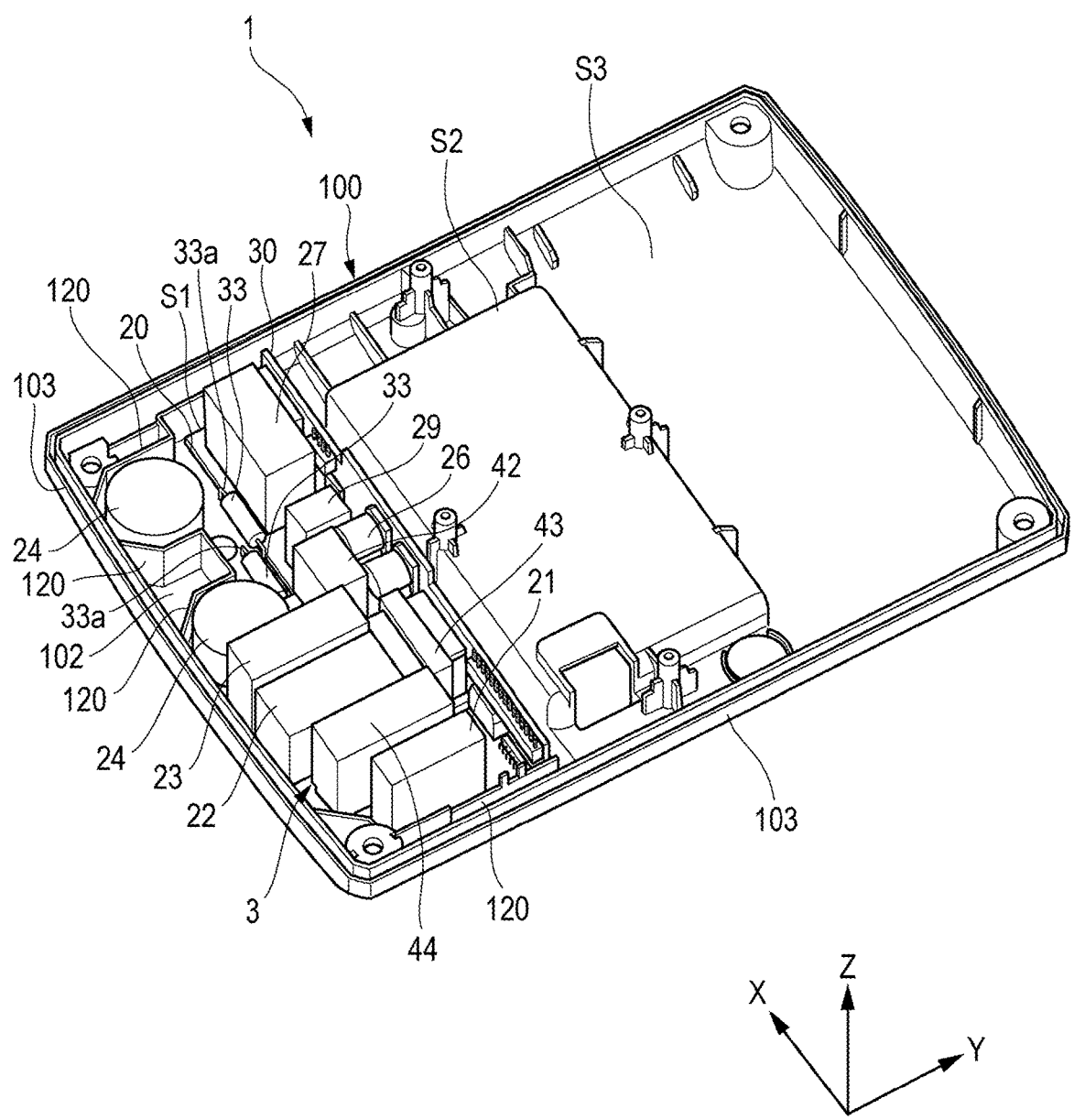
FIG. 3 is a view illustrating the high voltage generator housed in an outer housing before a potting material is injected into the outer housing.

Further, an X-axis direction, a Y-axis direction, and a Z-axis direction set for an AED 1 shown in FIG. 3 may be appropriately mentioned in the description of the embodiment. One of the X-axis direction, the Y-axis direction, and the Z-axis direction is perpendicular to the remaining two directions of the X-axis direction, the Y-axis direction, and the Z-axis direction.

Figure 1:
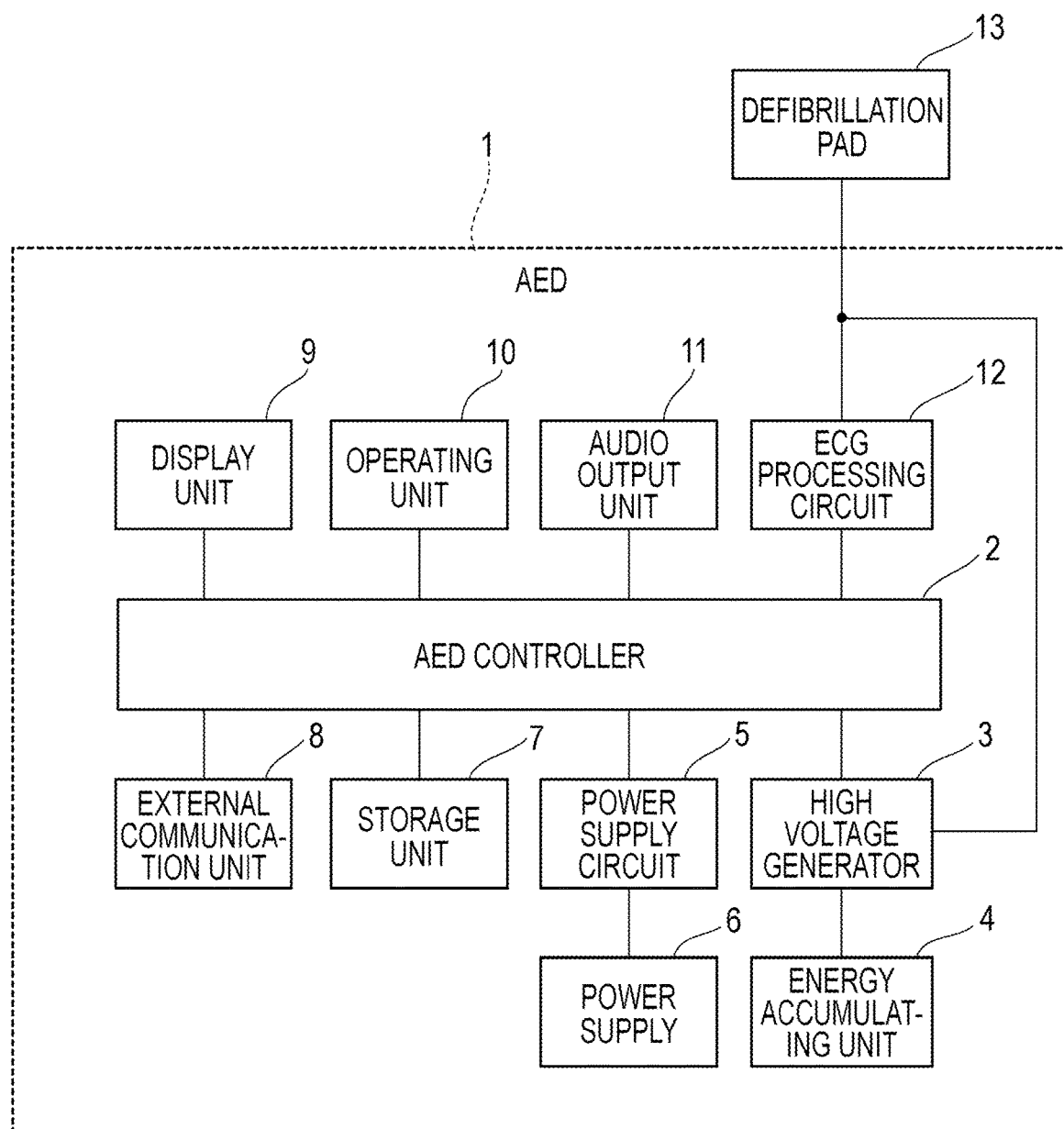
FIG. 1 is a block diagram illustrating a configuration of an automated external defibrillator (that will be hereinafter abbreviated to AED) according to an embodiment of the present disclosure (that will be hereinafter referred to as the present embodiment).

First, a configuration of the automated external defibrillator 1 (that will be hereinafter abbreviated to AED 1) will be described below with reference to FIG. 1. FIG. 1 is a block diagram illustrating the configuration of the AED 1 according to the present embodiment. As shown in FIG. 1, the AED 1 includes an AED controller 2, a high voltage generator 3, an energy accumulating unit 4, a power supply 6, a power supply circuit 5, a storage unit 7, and an external communication unit 8. The AED 1 further includes a display unit 9, an operating unit 10, an audio output unit 11, and an ECG processing circuit 12.

The AED 1 is a medical device that is configured to give an electric shock to a heart of a patient who has undergone cardiac arrest due to ventricular fibrillation, to thereby restore a function of the heart of the patient. The AED controller 2 is configured to control each of the constituent components provided in the AED 1. The AED controller 2 is, for example, constituted by a microcontroller including a processor and a memory, and an integrated circuit such as an ASIC (Application Specific Integrated Circuit). The processor includes, for example, at least one of a CPU (Central Processing Unit), an MPU (Micro Processing Unit), and a GPU (Graphics Processing Unit). The memory includes an ROM (Read Only Memory) and an RAM (Random Access Memory).

The high voltage generator 3 is configured to charge the energy accumulating unit 4 with electric energy for giving a patient (subject) an electric shock for defibrillation, and to discharge the electric energy accumulated in the energy accumulating unit 4. A specific configuration of the high voltage generator 3 will be described later. The energy accumulating unit 4 is configured to accumulate the electric energy for giving the patient the electric shock for defibrillation. For example, the energy accumulating unit 4 may be a high voltage film capacitor constituted by dielectric films.

The power supply 6 is a battery that is configured to supply electric power to the constituent components of the AED 1. For example, the power supply 6 is a lithium primary battery. The power supply circuit 5 is configured to convert a voltage of the power supply 6 into a voltage required for each of the constituent components of the AED 1. The power supply circuit 5 may be, for example, constituted by a switching regulator or a series regulator. The storage unit 7 is configured to store various programs for operating the AED 1, audio data, and electrocardiogram data of the patient. The storage unit 7 is, for example, constituted by a flash memory or a hard disk.

The external communication unit 8 is configured to transmit various data stored in the storage unit 7 to an external device or receive data from the external device. The external communication unit 8 may be an interface into which a connector of a wired cable such as an LAN cable is inserted, or may be a wireless communication module compatible with wireless communication standards such as Bluetooth (registered trademark) and Wi-Fi (registered trademark). When the external communication unit 8 is the wireless communication module, the external communication unit 8 may have a transmission/reception antenna, a high frequency circuit, and a signal processing circuit.

The display unit 9 is configured to display status of the AED 1 and vital data (such as the electrocardiogram data) of the patient to an operator. The display unit 9 may include, for example, an indicator for displaying the status of AED 1 such as a remaining battery level of the power supply 6, and a liquid crystal display for displaying an electrocardiogram waveform of the patient. The operating unit 10 is configured to accept an operation from the operator. For example, the operating unit 10 may include a power button for powering on the AED 1, and a shock button for giving the patient an electric shock. The audio output unit 11 may be a speaker that is configured to output voice guidance or a warning sound related to the operation on the AED 1.

The ECG processing circuit 12 is configured to process electrocardiogram signals outputted from two defibrillation pads 13 attached to the patient. For example, the ECG processing circuit 12 may have a differential amplifier that amplifies a difference between a potential signal outputted from one of the two defibrillation pads 13 and a potential signal outputted from the other defibrillation pad 13 to thereby generate electrocardiogram data, and an AD converter that converts the electrocardiogram data into digital data. The defibrillation pads 13 are detachably attached to the AED 1.

Figure 2:
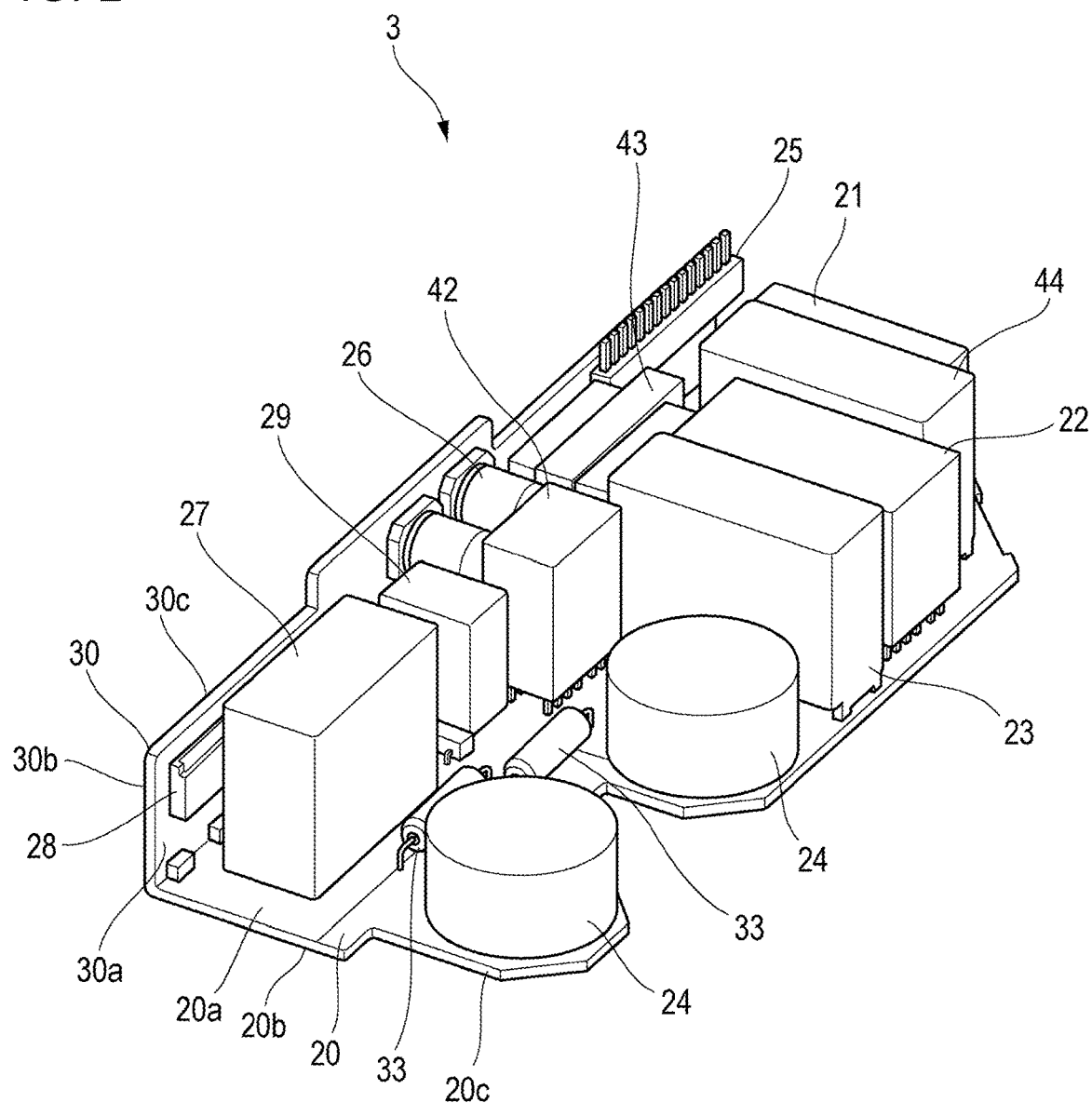
FIG. 2 is a perspective view illustrating a specific structure of a high voltage generator.

Next, the specific structure of the high voltage generator 3 according to the present embodiment will be described below with reference to FIG. 2. FIG. 2 is a perspective view illustrating the specific structure of the high voltage generator 3. As shown in FIG. 2, the high voltage generator 3 includes a high voltage circuit board 20, high voltage electronic components disposed on the high voltage circuit board 20, a relay circuit board 30, and relay electronic components disposed on the relay circuit board 30.

The high voltage circuit board 20 is a circuit board for generating electric energy (a biphasic discharge waveform) for giving the patient an electric shock. The high voltage circuit board 20 has a front face 20a, a back face 20b, and a side face 20c. The high voltage electronic components are disposed on the front face 20a. The back face 20b is located on an opposite side to the front face 20a. The side face 20c is located between the front face 20a and the back face 20b. As an example of the high voltage electronic components disposed on the high voltage circuit board 20, IGBT (Insulated Gate Bipolar Transistor) control transformers 21 and 29, a high voltage diode 44, and IGBTs (Insulated Gate Bipolar Transistors) 22 and 42, a film capacitor 23, a coil 24, a relay 27, internal discharge resistors 33, and a DC-DC transformer 43 are mounted on the high voltage circuit board 20. In the following description, these electronic components mounted on the high voltage circuit board 20 will be generically referred to as "high voltage electronic components" for convenience of description.

The relay circuit board 30 is a circuit board for relaying a signal outputted from the high voltage circuit board 20 or a signal to be inputted to the high voltage circuit board 20. The relay circuit board 30 is electrically connected to the high voltage circuit board 20. In the present embodiment, the relay circuit board 30 is physically connected to the high voltage circuit board 20. Incidentally, while the relay circuit board 30 is electrically connected to the high voltage circuit board 20, it should be noted that the relay circuit board 30 does not have to be physically connected to the high voltage circuit board 20. The relay circuit board 30 has a front face 30a, a back face 30b, and a side face 30c. The relay electronic components are disposed on the front face 30a. The back face 30b is located on an opposite side to the front face 30a. The side face 30c is located between the front face 30a and the back face 30b. The front face 30a of the relay circuit board 30 is substantially orthogonal to the front face 20a of the high voltage circuit board 20. As an example of the relay electronic components disposed on the relay circuit board 30, a high voltage output connector 28, an electrolytic capacitor 26, and a high voltage control connector 25 are mounted on the relay circuit board 30. In the following description, these electronic components mounted on the relay circuit board 30 will be generically referred to as "relay electronic components" for convenience of description.

Figure 4:
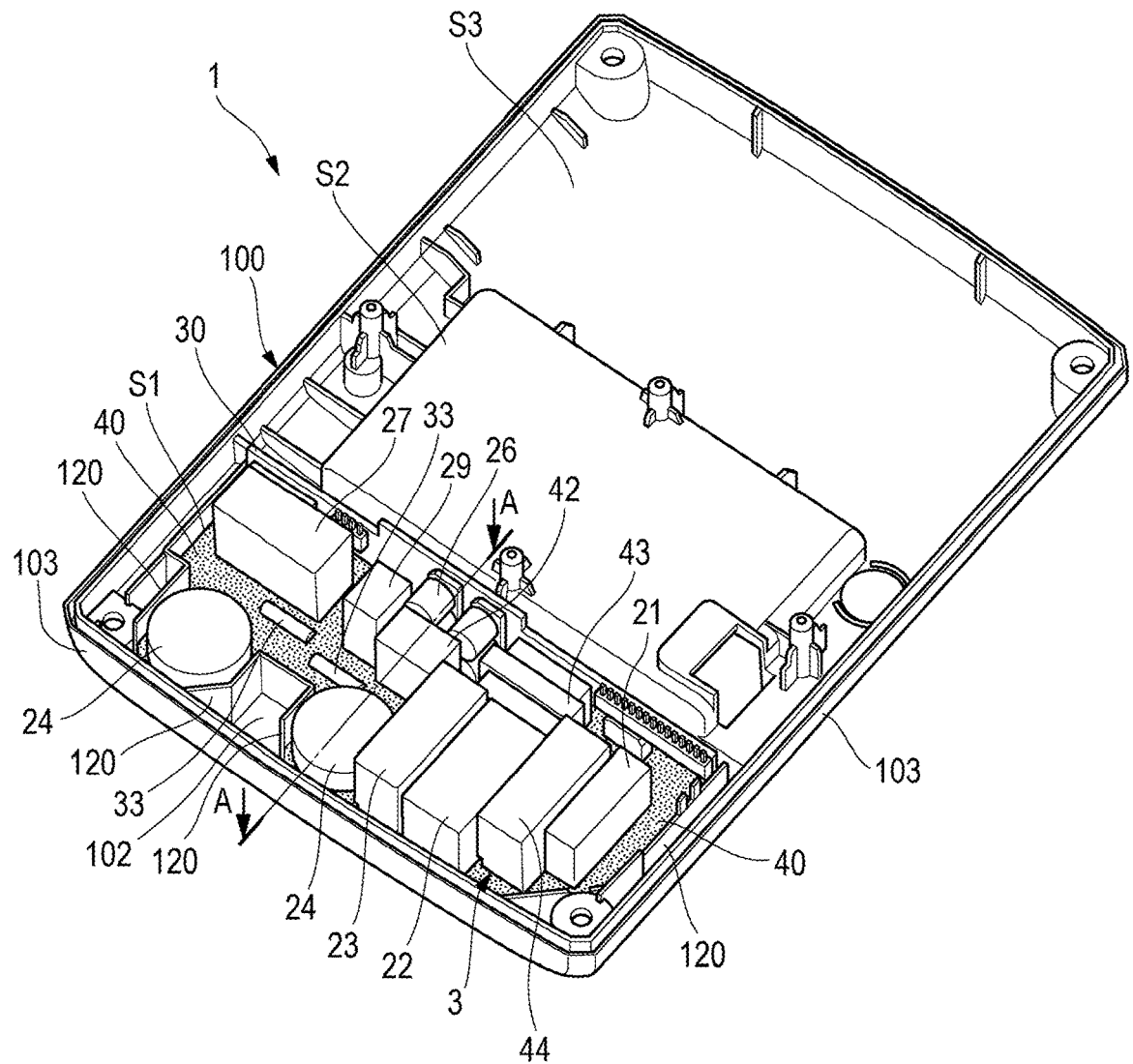
FIG. 4 is a view illustrating the high voltage generator housed in the outer housing after the potting material is injected into the outer housing.
Figure 4:
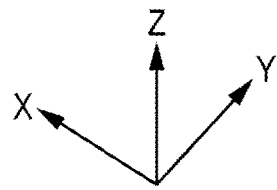
Figure 5:
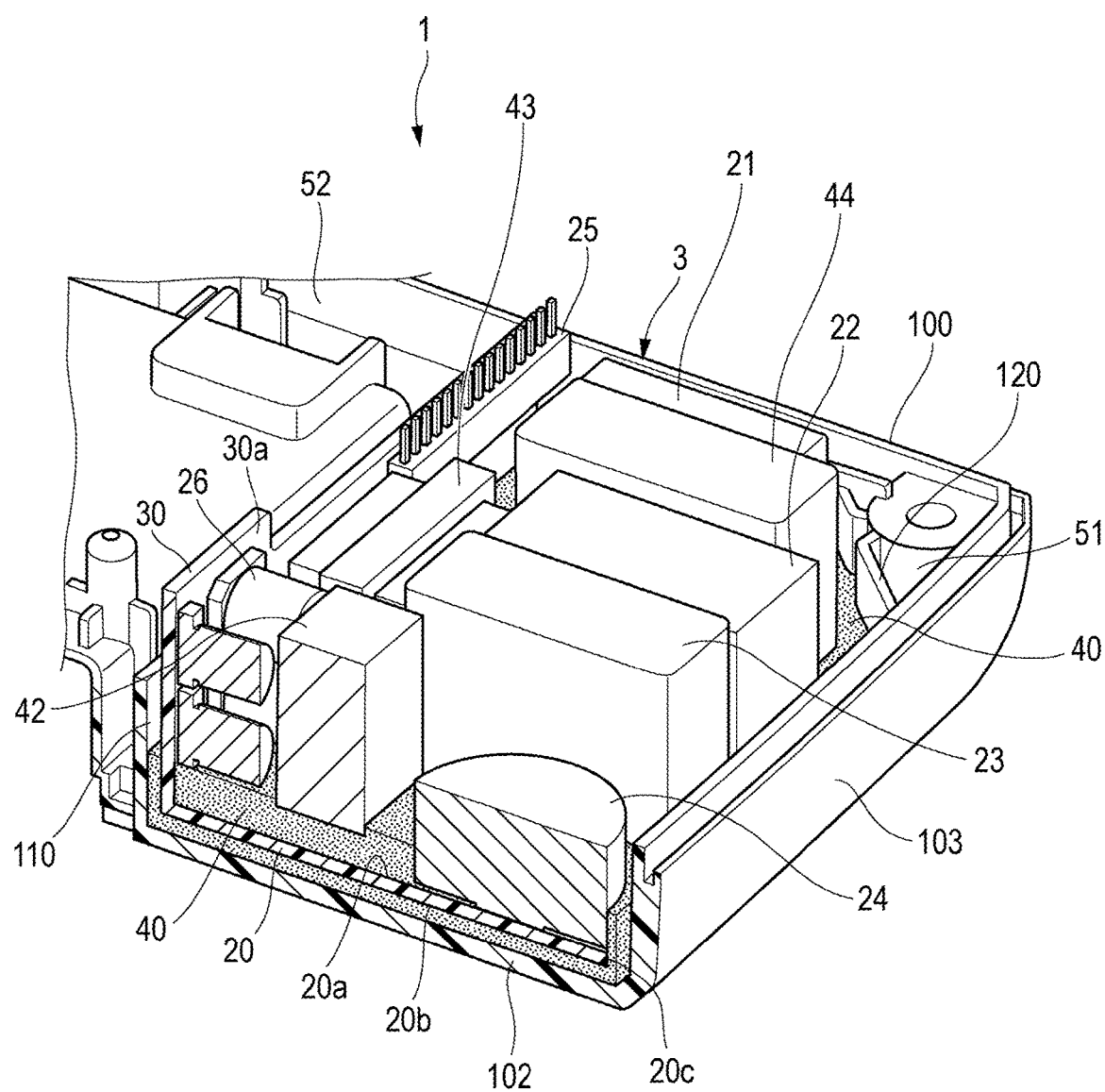
FIG. 5 is a perspective sectional view of the outer housing and the high voltage generator cut along a line A-A shown in FIG. 4.

Next, the high voltage generator 3 housed in an outer housing 100 that defines an exterior of the AED 1 will be described below with reference to FIGS. 3 to 5. FIG. 3 is a view illustrating the high voltage generator 3 housed in the outer housing 100 before a potting material 40 (see FIG. 4) is injected into the outer housing 100. FIG. 4 is a view illustrating the high voltage generator 3 housed in the outer housing 100 after the potting material 40 is injected into the outer housing 100. FIG. 5 is a perspective sectional view of the outer housing 100 and the high voltage generator 3 cut along a line A-A shown in FIG. 4. Although the other constituent components of the AED 1 shown in FIG. 1 than the high voltage generator 3 are also housed in the outer housing 100, illustration of these constituent components are omitted for convenience of explanation.

As shown in FIG. 3, the outer housing 100 is, for example, made of a resin material such as polycarbonate, an ABS resin, or a PBT resin. The outer housing 100 has three housing areas S1 to S3. The high voltage generator 3 and a partition plate 120 are housed in the housing area S1 (an example of a first housing area). A control board (not shown) including at least the AED controller 2 is housed in the housing area S2. The energy accumulating unit 4 (e.g. a high voltage film capacitor) is housed in the housing area S3.

The high voltage generator 3 is housed in the housing area S1 so that the back face 20b of the high voltage circuit board 20 faces a bottom face 102 of the outer housing 100. Further, the partition plate 120 is disposed inside the housing area S1 in the state in which the high voltage generator 3 is disposed in the housing area S1. The partition plate 120 may be, for example, made of the same resin material as the outer housing 100. The partition plate 120 that faces the side face 20c of the high voltage circuit board 20 is disposed between an outer wall portion 103 of the outer housing 100 and the side face 20c of the high voltage circuit board 20. In this respect, the partition plate 120 is disposed inside the housing area S1 so as to extend along at least a part of an outer shape of the high voltage circuit board 20.

In order to ensure electrical insulation among terminals of the high voltage electronic components disposed on the high voltage circuit board 20, the potting material 40 is cured after the potting material 40 is injected into the accommodation region S1 from the Z-axis direction in the state shown in FIG. 3. Thus, the high voltage generator 3 is partially covered with the potting material 40, as shown in FIG. 4 and FIG. 5.

In this respect, the potting material 40 covers the high voltage circuit board 20 and the terminals of the high voltage electronic components (e.g. terminals of the internal discharge resistors 33) disposed on the high voltage circuit board 20. In particular, while the terminals of the high voltage electronic components are completely covered by the potting material 40 from a viewpoint of ensuring the electric insulation, the high voltage electronic components are partially exposed from the potting material 40. While, for example, the terminals 33a of the internal discharge resistors 33 are completely covered with the potting material 40, as shown in FIG. 3 and FIG. 4, bodies of the internal discharge resistors 33 are partially exposed from the potting material 40. Further, the potting material 40 partially covers the relay circuit board 30.

Further, the potting material 40 is in contact with the high voltage circuit board 20 and the outer housing 100 so as to fix the high voltage circuit board 20 to the outer housing 100, as shown in FIG. 5. In particular, the front face 20a, the back face 20b, and the side face 20c of the high voltage circuit board 20 are completely covered with the potting material 40. Further, the potting material 40 contacts the partition plate 120 and the relay circuit board 30 to fix the partition plate 120 and the relay circuit board 30 to the outer housing 100. Specifically, the potting material 40 is filled in a space surrounded by the outer wall portion 103 of the outer housing 100, an inner wall portion 110 of the outer housing 100 that defines the housing area S1, the bottom face 102 of the outer housing 100, and the partition plate 120. The potting material 40 is in contact with the outer wall portion 103, the inner wall portion 110, and the bottom face 102 of the outer housing 100.

Further, the potting material 40 is filled between the side face 20c of the high voltage circuit board 20 and the outer wall portion 103 of the outer housing 100, between the back face 20b of the high voltage circuit board 20 and the bottom face 102 of the outer housing 100, and between the relay circuit board 30 and the inner wall portion 110 of the outer housing 100 respectively. Thus, the fixation between the high voltage circuit board 20 and the outer housing 100 can be made firm.

For example, an insulating material such as ceramics or an insulating resin may be used as the material of the potting material 40. Specifically, the potting material 40 may be formed out of an insulating resin such as an epoxy resin, a polybutadiene resin, a polyurethane resin, a silicone resin, an acrylic resin, or a polyester resin. In particular, a resin material high in adhesiveness to the outer housing 100 is preferred as the material of the potting material 40. The potting material 40 is preferably formed out of, for example, a resin containing polybutadiene as a main material.

According to the present embodiment, as described above, the high voltage circuit board 20 is directly fixed to the outer housing 100 by the potting material 40. Therefore, a dedicated housing for housing the high voltage circuit board 20 does not have to be separately provided in the outer housing 100, and a mechanical fixature (such as a screw or a rib structure) for fixing the dedicated housing and the outer housing 100 to each other does not have to be provided separately. Thus, the AED 1 can be miniaturized and durability of the AED 1 can be improved.

Further, the potting material 40 is in contact with the high voltage circuit board 20 and the outer housing 100. Accordingly, heat generated from the high voltage electronic components is efficiently conducted to the outer housing 100 through the high voltage circuit board 20 and the potting material 40. Thus, the heat generated from the high voltage electronic components can be efficiently dissipated to the outside of the AED 1, so that heat dissipation performance of the AED 1 can be improved. Therefore, the durability and the heat dissipation performance of the AED 1 can be improved, and the AED 1 can be miniaturized.

Further, while the terminals of the high voltage electronic components are completely covered with the potting material 40, the high voltage electronic components are partially exposed from the potting material 40 in the present embodiment. For example, while the terminals 33a of the internal discharge resistors 33 are completely covered with the potting material 40, the bodies of the internal discharge resistors 33 are partially exposed from the potting material 40. Therefore, it is possible to ensure the electrical insulation among the terminals of the high voltage electronic components by the potting material 40 while suppressing the filling amount of the potting material 40 with which the outer housing 100 is filled. Thus, the filling amount of the potting material 40 is suppressed so that the weight of the AED 1 can be reduced.

In the present embodiment, the partition plate 120 is provided between the side face 20c of the high voltage circuit board 20 and the outer housing 100 so as to extend along the part of the outer shape of the high voltage circuit board 20. Thus, the filling amount of the potting material 40 with which the outer housing 100 is filled can be suppressed, so that the weight of the AED 1 can be reduced.

In the present embodiment, the potting material 40 is filled between the back face 20b of the high voltage circuit board 20 and the bottom face 102 of the outer housing 100. Therefore, the high voltage circuit board 20 and the outer housing 100 can be surely fixed to each other through the potting material 40, and the heat generated from the high voltage electronic components can be efficiently dissipated to the outside of the AED 1. Therefore, the heat dissipation performance of the AED 1 can be improved.

Further, in the present embodiment, the front face 30a of the relay circuit board 30 and the front face 20a of the high voltage circuit board 20 are substantially orthogonal to each other. Accordingly, an outer shape of the high voltage generator 3 can be miniaturized. Thus, the housing area S1 of the outer housing 100 where the high voltage generator 3 is housed can be reduced, so that an outer shape of the AED 1 can be miniaturized.

Although the embodiment of the present disclosure has been described above, the technical scope of the present disclosure should not be interpreted limitedly by the description of the present embodiment. The present embodiment is merely exemplar, and it is going to be understood by those skilled in the art that various changes can be made on the embodiment within the scope of the disclosure described in the scope of claims. The technical scope of the present disclosure should be determined based on the scope of the disclosure described in the scope of claims and the scopes of equivalents thereof.

For example, the high voltage electronic components are mounted on the high voltage circuit board 20 in the present embodiment. However, the number of the high voltage electronic components mounted on the high voltage circuit board 20 may be one. Similarly, the number of the relay electronic components mounted on the relay circuit board 30 may be one.

Further, the high voltage generator 3 has the high voltage circuit board 20 and the relay circuit board 30 in the present embodiment. However, the high voltage generation unit 3 does not have to have the relay circuit board 30. In this case, the high voltage electronic components and the relay electronic components may be mounted on the high voltage circuit board 20.

The invention claimed is:

1. An automated external defibrillator comprising:
a high voltage generator configured to charge or discharge electric energy for giving a subject an electric shock for defibrillation;
an outer housing configured to house the high voltage generator and defining an exterior of the automated external defibrillator; and
a potting material containing an insulating material,
wherein the high voltage generator comprises:
a high voltage circuit board;
a high voltage electronic component disposed on the high voltage circuit board, and
wherein the potting material covers the high voltage circuit board and a terminal of the high voltage electronic component, the terminal connecting the high voltage circuit board and the high voltage electronic component, and is in contact with the high voltage circuit board and the outer housing to fix the high voltage circuit board to the outer housing, and
the terminal of the high voltage electronic component is completely covered with the potting material, and the high voltage electronic component is partially exposed from the potting material.

2. The automated external defibrillator according to claim 1,
wherein the high voltage circuit board comprises:
a front face on which the high voltage electronic component is disposed;
a back face that is located on an opposite side to the front face; and
a side face that is located between the front face and the back face,
wherein the automated external defibrillator further comprises:
a partition plate that faces the side face of the high voltage circuit board and that is disposed between the outer housing and the side face of the high voltage circuit board, and
wherein the potting material is in contact with the partition plate.

3. The automated external defibrillator according to claim 2, wherein
the partition plate is disposed to extend along at least a portion of an outer shape of the high voltage circuit board.

4. The automated external defibrillator according to claim 1, wherein
the outer housing has a first housing area where the high voltage generator is housed, and
the potting material is in contact with an inner wall portion of the outer housing defining the first housing area.

5. The automated external defibrillator according to claim 1, wherein
the potting material is made of a resin containing polybutadiene as a main material.

6. The automated external defibrillator according to claim 1,
wherein the high voltage circuit board comprises:
a front face on which the high voltage electronic component is disposed;
a back face that is located on an opposite side to the front face; and
a side face that is located between the front face and the back face, and
wherein the potting material is provided between the back face of the high voltage circuit board and the outer housing.

7. An automated external defibrillator comprising:
a high voltage generator configured to charge or discharge electric energy for giving a subject an electric shock for defibrillation;
an outer housing configured to house the high voltage generator and defining an exterior of the automated external defibrillator; and
a potting material containing an insulating material,
wherein the high voltage generator comprises:
a high voltage circuit board; and
a high voltage electronic component disposed on the high voltage circuit board, and
wherein the potting material covers the high voltage circuit board and a terminal of the high voltage electronic component, and is in contact with the high voltage circuit board and the outer housing to fix the high voltage circuit board to the outer housing,
wherein the high voltage generator further comprises:
a relay circuit board that is physically and electrically connected to the high voltage circuit board; and
a relay electronic component disposed on the relay circuit board,
wherein a front face of the relay circuit board on which the relay electronic component is disposed is substantially orthogonal to a front face of the high voltage circuit board on which the high voltage electronic component is disposed, and
wherein the potting material partially covers the relay circuit board.

* * * * *